United States Patent [19]

Kronner

[11] Patent Number: 5,571,072
[45] Date of Patent: Nov. 5, 1996

[54] DUAL-AXIS ENDOSCOPE HOLDER

[76] Inventor: Richard F. Kronner, 1443 Upper Cleveland Rapids Rd., Roseburg, Oreg. 97470

[21] Appl. No.: 430,346

[22] Filed: Apr. 28, 1995

[51] Int. Cl.$^6$ ................................................. A61B 19/00
[52] U.S. Cl. ........................... 600/102; 600/228; 600/229; 248/279.1
[58] Field of Search ................................ 600/227–230, 600/102; 128/DIG. 26; 248/278.1, 279.1

[56] References Cited

U.S. PATENT DOCUMENTS

| | | |
|---|---|---|
| 4,573,452 | 3/1986 | Greenberg. |
| 4,863,133 | 9/1989 | Bonnell. |
| 5,224,680 | 7/1993 | Greenstein et al.. |

OTHER PUBLICATIONS

Stoney, Ronald J., M.D., F.A.C.S., "How to Acheive Optimum Exposure of the Upper Abdominal Aorta and Its Branches", Dec. 1986, Minnesota Scientific, Inc. 3939 Chandler Dr., Minneapolis, MN 55421–4497 pp. 1–4.
Computer Motion, Inc., 250 Storke Rd., Ste. A., Goleta, CA 93117, "Enhancing Performance Through Robotics", and Robotic Enhancement Technology, 1 sheet.
Leonard Medical, Inc., 1464 Holcomb Rd., Huntingdon Valley, PA 19006 featuring literature on the Leonard Arm, Leonard Arm, Jr. Laparoscope Holder and Instrument Holder, Oct. 20, 1993 or earlier as noted, 11 pages.
Omni–Tract Surgical literature on Corral Retractor, undated Omni–Lapotract System 1993 and Omni–Tract Accessories, 1991, 403 County Rd. E2 West, St. Paul; MN 55112–6858 –3 sheets.
Omni–Tract Surgical Catalog featuring System Components, Retractors and Blades and Accessories, 1991. Address: 403 County Rd. E2 West, St. Paul MN 55112–3237, 8 pages.
Computer Motion, Inc. 250 Storke Rd., Suite A, Goleta, CA93117 "Aesop: Automated Endoscopic System for Optimal Positioning", 4 pages, undated.
Cuschieri, Alfred, M.D., "Minimal Access Surgery and the Future of Interventional Laparascopy", The American Journal of Surgery, vol. 161, Mar. 1991, pp. 404–407.
NASA Tech Briefs, "Robotics For Safer Surgery", Jan. 1994, vol. 18, No. 1, pp. 16–18.
Nathanson et al., "Laparoscopic Cholecystectomy", Br. J. Surg. vol. 78, No. 2, Feb. 1991, pp. 155–159.
Literature of the Stoney Mini Vascular Retractor System–VM100, Omni–Tract Surgical, Nov. 1991, 4 pages (2 sheets).
The Iron Intern Robotic Retractor—Your Most Dependable Assistant–1 sheet with photograph of same, undated.
Berci et al. "New Ideas and Improved Instrumentation for Laparoscopic Cholecystectomy", *Surgical Endoscopy*, vol. 5, 1991, pp. 1 and 3.

*Primary Examiner*—Richard J. Apley
*Assistant Examiner*—Kelly McGlashen
*Attorney, Agent, or Firm*—Edward B. Anderson

[57] ABSTRACT

A cannula and associated endoscope are secured to an operating table by a mechanical linkage assembly having linear and angular connections. These connections are adjustable for supporting an endoscope extending through an incision. Two angular connections are friction joints that allow manual repositioning of the scope by pivoting about respective orthogonal axes that intersect at a point along the scope that is coincident with the location of the incision.

14 Claims, 5 Drawing Sheets

DUAL-AXIS ENDOSCOPE HOLDER

BACKGROUND OF THE INVENTION

1. Field of the Invention

This invention relates to structure for supporting a surgical instrument, such as an endoscope, and more particularly to such structure which provides for repositioning of the instrument during surgery without stressing an incision through which the instrument extends.

2. Related Art

Laparoscopic surgery is a procedure in which surgical instruments and a viewing scope, referred to generally as an endoscope and more specifically as a laparoscope, are inserted through respective small puncture wounds or incisions into the abdominal cavity of a patient. A small video camera is attached to the laparoscope and connected to a television monitor for viewing the procedure.

The instruments and the laparoscope are inserted through cannulae which are first inserted through the incisions. Cannulae are hollow tubes with gas valves. The cannulae are left in the puncture wounds throughout the procedure. This allows the instruments and scope to be removed and reinserted as necessary.

To aid in visualizing the intraabdominal structures, gas is inserted through one of the cannulae to raise the abdominal wall. Seals are required at the exit points of the scope and instruments to prevent the gas from escaping.

The viewing laparoscope is inserted through a cannula which is usually inserted through an incision made in the umbilicus. The scope is then directed toward the pelvis for pelvic surgery or toward the liver for gallbladder surgery.

Throughout the procedure it is necessary for the surgeon, assistant surgeon, or a scrub nurse to hold the scope and direct it at the target of the surgery. It is constantly being repositioned to obtain the best view. This process ties up one hand of the surgeon or assistant surgeon, if either holds the scope. The scrub nurses also have other tasks to perform, and holding the scope interferes with performing these tasks. It is also difficult for the surgeon to direct others to position the scope for the best view. When the scope is not held by the surgeon, it is often misdirected.

The support of a laparoscope has been provided through the use of robotic retractors. Retractors hold instruments in fixed positions, such as for holding an incision open to allow a surgeon access to the underlying body parts. The retractors are fixedly clamped to a mechanical skeleton. This skeleton has also been used to hold a laparoscope in a fixed position. When it is desired to move the scope, the clamp must be readjusted, and also the skeleton linkages must usually also be adjusted to accommodate a change in angle of insertion of the laparoscope.

An apparatus that accommodates changes more readily is a robot-like arm having ball joints next to an instrument holder. This apparatus is sold under the proprietary name The Leonard Arm by Leonard Medical, Inc. of Huntingdon Valley, Penn., and is described in U.S. Pat. No. 4,863,133 issued to Bonnell. Two articulating arms are used to couple an instrument clamp to the operating table rail. A vacuum supply is used to frictionally hold the joints. Three joints provide three degrees of freedom of movement. When not freely moveable, manual force on the instrument clamp is sufficient to reposition the instrument.

The invention of Bonnell is intended as a general-purpose instrument holding apparatus. As such it is up to the user to control movement of the instrument supported on the apparatus, since the axes of movement are independent of and spaced from the patient, except for ball joints next to the instrument holder. Further, this apparatus presents two arms that extend upwardly over the operating table which interfere with access to the patient by attendants, and requires a dedicated vacuum source in the operating room.

A less imposing and more technically sophisticated robotic arm that is commercially available is sold under the name AESOP by Computer Motion, Inc. of Goleta, Calif. This arm has servo-operated joints with computer-controlled motion based on a multipedal foot-operated input device. This device has articulation about axes that are also spaced from the endoscope, thereby requiring very careful movement control by the surgeon in order to avoid stressing the tissue adjacent the laparoscope incision. Further, the computer used to control movement makes the system very expensive to produce.

A less expensive manual apparatus is described in U.S. Pat. No. 4,573,452 issued to Greenberg. A rigid metal ring that surrounds the incision area is mounted above the table. A vertical control arm is mounted on a ball-and-socket joint along the metal ring. A tensionable cable-like component connects the top of the control arm to a laparoscope holder. After initial placement of the holder, the cable-like component is secured, after which movement of the laparoscope is achieved by pivoting the control arm about the ball and socket joint. It is suggested that the ball and socket joint be coplanar with the incision through which the laparoscope extends.

The Greenberg apparatus requires the use of the ring which is positioned over the patient. This ring, though of low profile can interfere with surgical procedures. Further, the laparoscope is pivoted about the ball-and-socket joint which is located along the ring. Thus, except for movement of the scope about the axis that intersects both the incision and joint, the laparoscope moves from the incision, causing stress on the tissue around the incision. Significant changes in position of the scope requires release and repositioning of the cable-like component.

SUMMARY OF THE INVENTION

The present invention overcomes disadvantages of these prior art devices. Generally, the present invention provides an endoscope holder apparatus that provides for adjustment of the endoscope, once it is positioned through an incision, without stressing the tissue surrounding the incision.

More specifically, the present invention provides an endoscope holder apparatus having a base fixedly mountable on an external frame, such as a surgical table. A holder is fixedly mountable to the endoscope for supporting the endoscope along a longitudinal scope axis that extends through an incision region. An articulating assembly couples the base to the holder for limiting movement of the holder to motion about first and second non-parallel axes that pass through the incision region.

The preferred embodiment of the invention includes a first clamp fixedly mountable at a position along a mounting rail of a surgical table. A second clamp fixedly secures a first arm in a selected vertical position relative to the first clamp and in a selected orientation about a vertical first axis. A third clamp, having a clamp body is mounted on the upper end of the first arm for fixedly securing the clamp body about a horizontal second axis.

A first manually operable friction pivot joint is mounted on the third clamp for pivoting a second arm about a third axis that is orthogonal to the first axis when the third axis is horizontal. A fourth clamp fixedly secures the second arm in a selected position along the third axis.

A holder is fixedly mountable to an endoscope for holding the endoscope along a scope axis that intersects the third axis at a pivot point. Finally, a second manually operable friction pivot joint is mounted on an end of the second arm so that it is spaced from the third clamp. The second pivot joint is selectively manually attached to the holder for pivoting the holder relative to the second arm about a fourth axis that is orthogonal to and intersects the third axis at the pivot point.

The pivot joints allow for manually pivoting an endoscope supported in the holder about the pivot point when the first, second, third and fourth clamps are secured. By having the two adjustable pivot axes intersect the scope axis in the incision region, any movement of the scope will result in minimal movement in the incision region. Since the incision is typically as small as possible, this invention thus assures that there is no excessive stress on the tissues surrounding the incision. Further, in its preferred form in which the pivots are frictionally set, a supported endoscope is held in position by the apparatus when the attending surgeon releases hold of it. Further, the surgeon can reposition it manually by overcoming the frictional forces. Those forces are adjustable to accommodate supporting endoscopes having different weights.

These and other features and advantages of the present invention will be apparent from the preferred embodiment described in the following detailed description and illustrated in the accompanying drawings.

DETAILED DESCRIPTION OF THE PREFERRED EMBODIMENT

Figure 1:
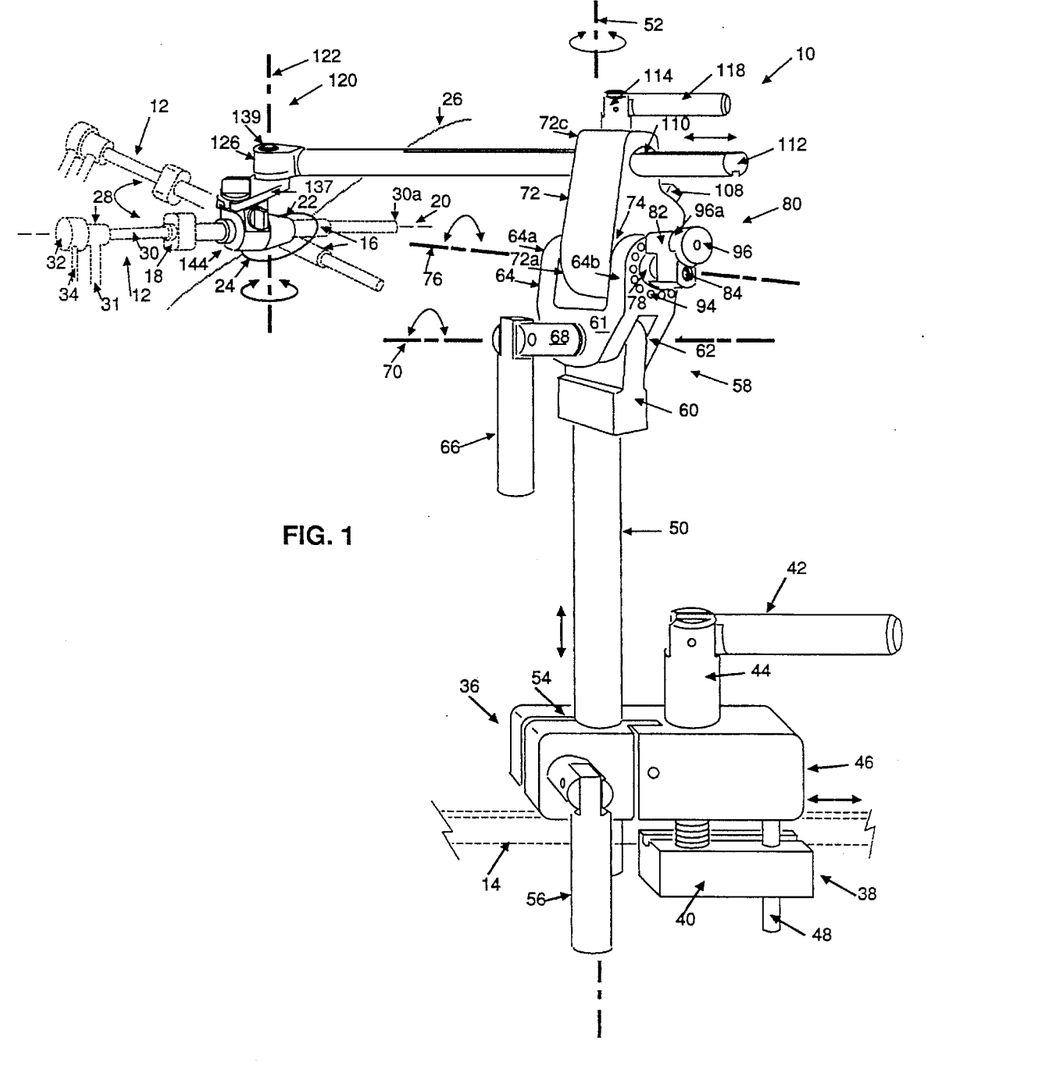
FIG. 1 is a an isometric view of an apparatus made according to the invention.

Referring initially to FIG. 1, an apparatus 10 is shown for supporting a conventional laparoscope 12 relative to an operating table having an equipment mounting rail 14. The term endoscope as used herein also refers to associated equipment, such as a cannula 16. The cannula has a gas valve 18 for preventing the leakage of gas from around the shaft of the laparoscope. The tubular end of the cannula extends along a scope axis 20 through an incision 22 located in what is generally referred to as an incision region 24 of a patient 26.

The laparoscope includes an eyepiece 28 mounted on the end of a viewing tube 30 which extends along axis 20 to an end 30a. Light received from a light source is transmitted to tube 30 via an optical cable 31. The light is directed out of tube end 30a for illuminating the body cavity. The body cavity is then viewed by a video camera 32 connected to a monitor by a connecting cable 34.

Apparatus 10 includes a base 36 having a base clamp 38 with a jaw 40. Manual turning of a lever 42 screws a clamp shaft 44 for moving the jaw relative to a base member 46. A guide pin 48 and shaft 44 maintain the orientation of the jaw relative to rail 14.

A vertical shaft 50 is rotatable about and shiftable along a first vertical axis 52 in an elevation clamp 54 securable by a handle 56. At the top of shaft 50 is a tilt clamp 58, including a fixed member 60 fixedly extending upwardly from the shaft, and a pair of jaws 61 and 62 formed in a lower support body 64. Jaws 61 and 62 are secured on fixed member 60 by a lever 66 that is used to drive a clamp shaft 68. Clamp 58 is used to secure lower support body 64 about a first horizontal axis 70 defined by shaft 68.

Figures 2, 3:
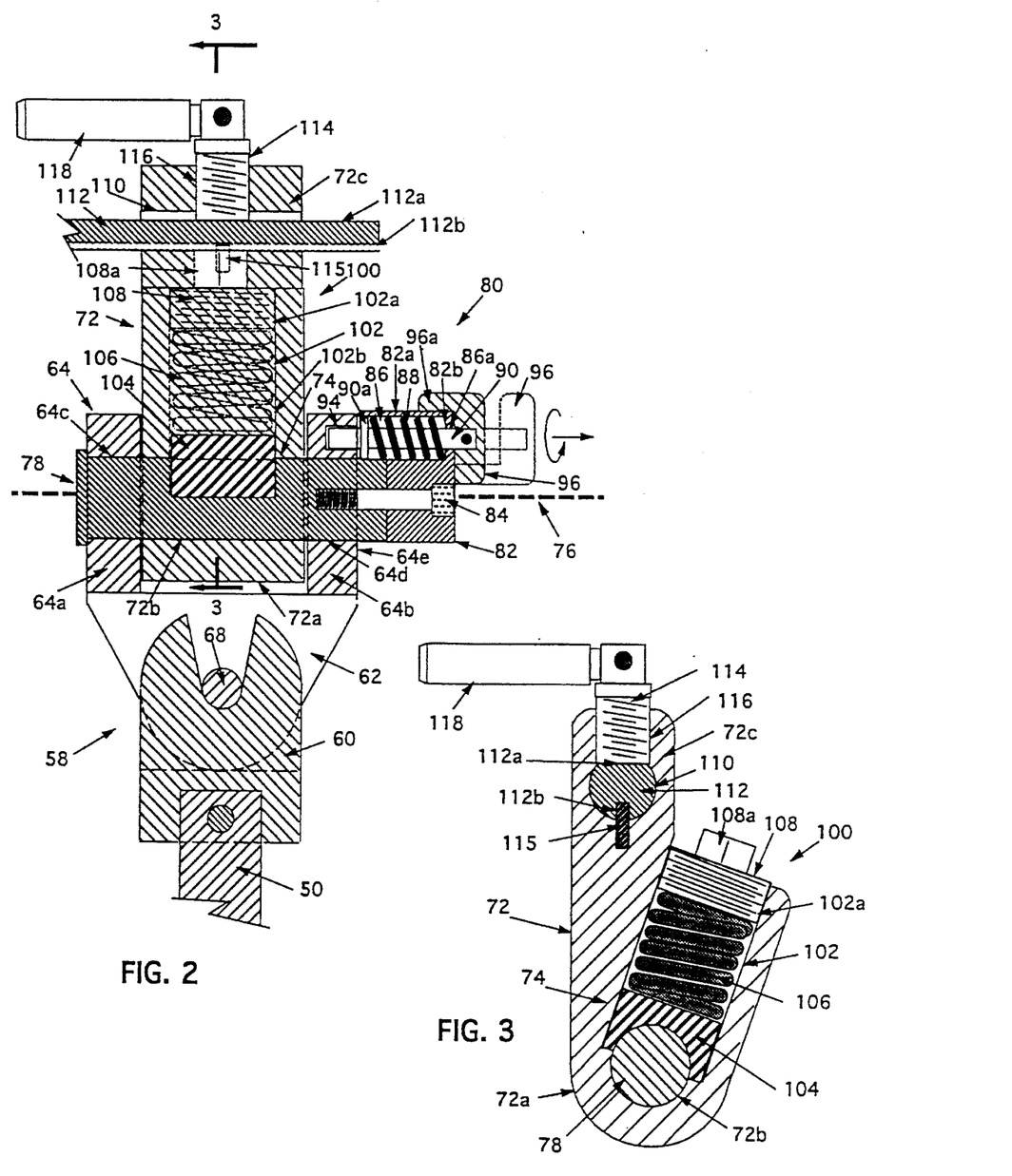
FIG. 2 is a cross section of a first frictional pivot joint of the apparatus of FIG. 1 taken along a vertical plane containing the pivot axis.
FIG. 3 is a cross section taken along line 3—3 in FIG. 2.

As shown more clearly in FIGS. 2 and 3, lower support body 64 and an upper support body 72 form part of a first frictional pivot joint 74, also referred to as articulating means, providing pivoting about a pivot axis 76. When lower support body 64 is in an upright position, as shown in the figures, axis 76 is also horizontal, and therefore is referred to as a horizontal axis even though it is not always horizontal.

Support body 64 includes two of upstanding, spaced-apart shoulders 64a and 64b. These shoulders have respective bores 64c and 64d sized to slidingly receive a solid shaft element 78 for rotation about axis 76. Element 78 is also generally referred to as a movement member.

A friction lock assembly 80 selectively fixes the position of shaft element 78 relative to lower support body 64. Assembly 80 includes a shaft extension 82 fixedly attached to shaft element 78 by a threaded bolt 84. Extension 82 has an eccentric arm 82a that extends adjacent to face 64e.

A bore 86 extends through arm 82a along an axis that is parallel with pivot axis 76. Bore 86 is sized to receive a compression spring 88 that seats against a shoulder 82b formed by a reduced-diameter bore portion 86a. The end of spring 88 adjacent to face 64e is seated on a ring or flange 90a of a pin 90. In the position shown in FIG. 2, one end of pin 90 extends freely into one of a series of cavities 94 extending into support body 64 through face 64e. Cavities 94 are distributed circumferentially around shaft element 78.

The opposite end of pin 90 extends through reduced-diameter bore portion 86a and is fixedly attached to a friction release knob 96. Knob 96 includes a leg 96a that extends along the side of extension 82. Leg 96a has a length that is slightly longer than the length of pin 90 that extends into cavity 94.

When pin 90 extends into cavity 94, as shown in FIG. 2, the position of shaft element 78 is fixed relative to lower support body 64. When knob 96 and attached pin 90 are manually pulled away from face 64e, as shown by the axial arrow, shaft element 78 is freely pivotable with respect to body 64. Knob 96 may be rotated about pin 90 when the pin is retracted from a cavity, positioning leg 96a on the outer end of extension 82, as shown by the position of the knob in phantom lines. This retains the pin out of the cavities, leaving shaft element 78 to freely rotate relative to body 64. When it is desired to fix the position of the shaft element relative to the lower support body, it is simply necessary to rotate leg 96a until it is oriented away from the end of the extension. The shaft extension is then rotated as needed in order to align pin 90 with a cavity 94. Spring 88 then drives the end of the pin into the cavity, again locking the rotational position of the shaft element relative to the lower support body.

Upper support body 72 has a lower end 72a positioned between shoulders 64a and 64b. A bore 72b coaxial with bores 64c and 64d, slidingly receives shaft element 78. Both the upper and lower support bodies thus pivot with respect to each other and with respect to the shaft element (subject to the operation of lock assembly 80).

A friction assembly 100, also referred to as movement-resisting means, is mounted in a bore 102 in upper support body 72 for applying friction for resisting pivoting of body 72 relative to shaft element 78. Bore 102 has an upper end 102a that is open and threaded, and a lower end 102b that is open to shaft element 78. A saddle-shaped friction bushing 104 conforms to and rides on shaft element 78 in bore 102. A compression spring 106 is positioned in bore 102 between bushing 104 and a spring-tension adjustment screw 108.

Screw 108 is threadedly received in upper end 102a of bore 102 and has an externally extending hexagonal knob 108a used to turn screw 108, and thereby adjust the force of spring 106 on bushing 104. This in turn adjusts the friction between bushing 104 and shaft element 78.

An upper end 72c of the upper support body has a channel 110 that extends parallel to pivot axis 76. Channel 110 is cylindrical. A cross bar 112, generally conforming to the shape of channel 110 except for an upper flat edge 112a and a lower groove 112b, extends slidingly through the channel. Bar 112 is selectively secured in position relative to body 72 by a clamp in the form of a lock screw 114 that is threadedly received in a vertical bore 116 that extends into channel 110. A pivotable handle 118 is used to manipulate screw 114. A pin 115 is fixed in a reduced diameter bore in body 72 such that one end of the pin extends into groove 112b of bar 112. This prevents bar 112 from turning in channel 110, but allows movement of the bar through the channel.

One end of bar 112 extends through body 72, as shown in FIG. 2. The other end supports a second friction joint 120 that provides for pivoting about a vertical pivot axis 122 that is orthogonal to pivot axis 76, and intersects axis 76 at a point 124. As will be seen, point 124 is in incision region 24, and preferably also is on scope axis 20. However, the advantages of the present invention are substantially obtained so long as axes 76 and 122 both pass through the incision region, whether or not they intersect.

Joint 120 includes a joint body 126 mounted to bar 112 by a pin 128 passing through the body and a bar extension 112a extending into a cavity 130. Spaced from cavity 130 is a vertical bore 132 having a wide upper section 132a, a narrow lower section 132b, and a tapered intermediate section 132c. A pivot shaft 134 is positioned in bore 132 and is sized and shaped to generally conform to the lower end of bore section 132a, as well as sections 132b and 132c, as shown. Shaft 134 rotates within the bore and has a distal end 134a extending out from the bottom of bore 132. End 134a extends fixedly into a conforming hole 136 in an elongate arm 137. Joint 120 thus provides pivoting of arm 137 about vertical pivot axis 122.

A compression spring 138 is disposed in bore 132 in contact with the top of shaft 134. The force of the spring is controlled by adjustment of a screw 139 threadedly received in the top of upper bore section 132a. As with screw 108, screw 139 has a hexagonal adjustment knob 139a engageable by a wrench for rotating the screw. Since no weight is supported by joint 120, only moderate spring pressure is required to hold scope holder 144 in position. This frictional drag is readily overcome by manually applying a minimum force to holder 144.

Figure 4:
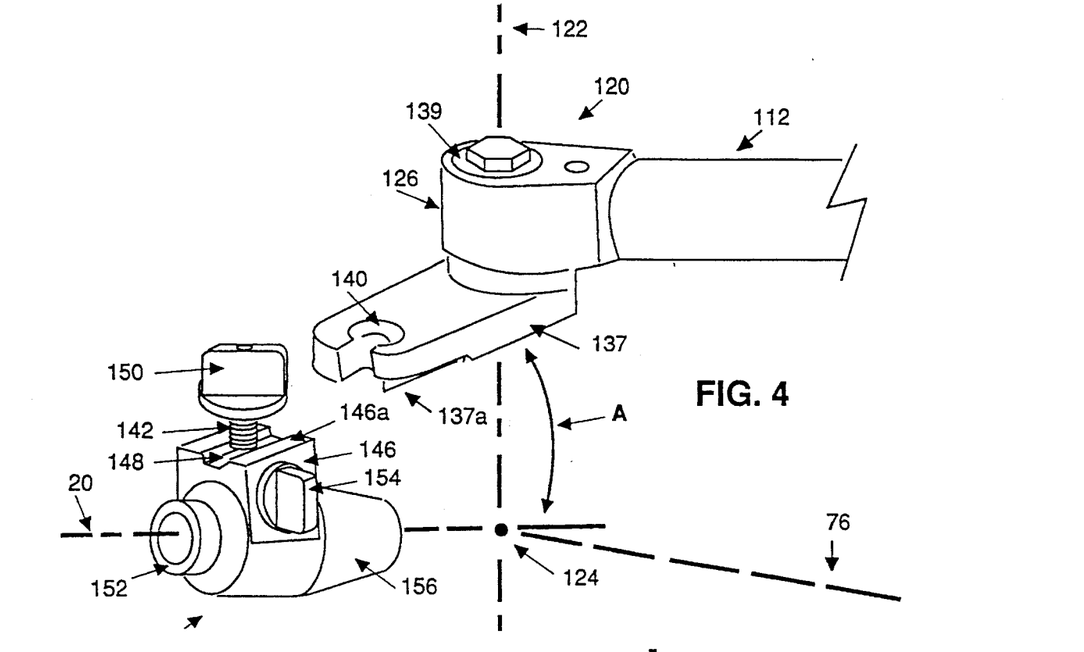
FIG. 4 is an enlarged isometric view of a second frictional pivot joint and endoscope holder of the apparatus of FIG. 1.

Arm 137 extends horizontally from axis 122 and has an end opposite from the axis with a bore 140 that is open along one side, as is shown in FIG. 4. This opening receives a threaded shank 142 of a quick-release scope holder 144. Holder 144 includes a main body 146 having a horizontal channel 148 in a top surface 146a. A connection knob 150 rotates on shank 142 for joining holder 144 to arm 137. The arm has a bottom surface 137a that conforms with channel 148, so that main body 146 is fixed in alignment with arm 137 when holder 144 is attached to the end of the arm.

Body 146 also has a cannula passageway, not shown, extending along scope axis 20. Axis 20 is at an angle A of 20° from horizontal, and as has been mentioned, extends through incision region 24, and preferably intersects both axes 76 and 122 at point 124. Attached to body 146 opposite from point 124 is an annular gas seal 152 that seals the main body relative to a cannula 16 supported therein. This keeps intra-abdominal gas from escaping between the holder and the cannula. A depth lock knob 154 is joined to a cam lock, not shown, that secures the penetration position of the cannula.

Figure 5:
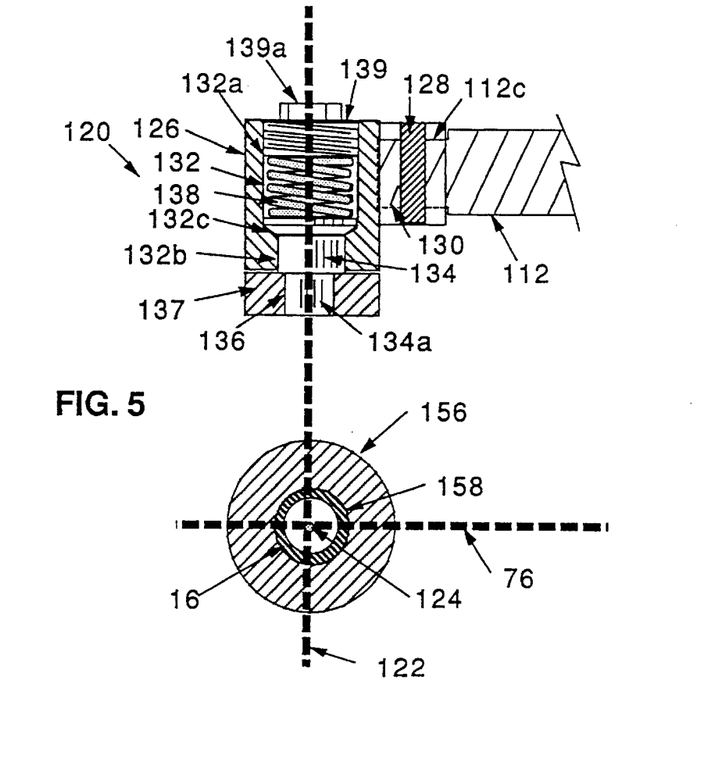
FIG. 5 is a cross section of the joint and holder of FIG. 4 taken through the pivot axis of the joint.

A scope holder extension 156 is joined to main body 146. This extension is preferably cone shaped, tapering toward the incision region. Extension 156 has a passageway 158, shown in FIG. 5 that conforms with the passageway in the main body of the holder, and correspondingly extends along axis 20. The extension is preferably long enough to extend through incision region 24. This means that horizontal axis 76 and vertical axis 122 extend through the extension and point 124 is inside passageway 158, as shown in the figure. Other suitable devices may also be used to connect apparatus 10 to an endoscope.

During initial setup, the position of base clamp 38 along operating side rail 14 is selected so that cross bar 112 can be positioned close to the patient without obstructing the operating procedure. A cannula 16 is inserted into holder 144 and the cannula is inserted into the abdominal cavity using standard techniques. If large areas of the abdomen are to be visualized, it is important to do so prior to attaching holder 144 to arm 137.

The position of arm 137 is aligned with holder 144 by movement of arm 112 in channel 110, movement of shaft 50 in base 36, and movement of base 36 along rail 14. Base 36 is secured on the rail by tightening clamp 38. The vertical position of shaft 50 is then secured by locking elevation clamp 54, and the position of the cross bar is secured by tightening lock screw 114. Holder 144 is then secured on the end of arm 137, as shown in FIG. 1.

If necessary, the angle of cross bar 112 relative to vertical shaft 50 may be adjusted using tilt clamp 58. Clamp 58 should be loose when the position of vertical shaft 50 is being set, since the angle of the cross bar and the position of the cross bar relative to the patient affect the position of the vertical shaft.

For ease of set up, when large movements are being made, knob 96 of the friction lock assembly is pulled out and rotated so that leg 96a rests on the outer face of the shaft extension, holding pin 90 out of cavities 94. There is then no resistance to movement between lower and upper support bodies 64 and 72. Lock assembly 80 thus disables friction assembly 100. When the desired position of the upper support body is reached, knob 96 is simply rotated back to its original position and shaft extension 82 is rotated until pin 90 finds a cavity. Joint 74 is then a friction joint that can be manipulated by applying a sufficient force to a laparoscope held in holder 144.

During use, to move the angle of the scope and cannula through the incision, the scope is grasped at a convenient location and moved. The scope is only movable or articulatable about horizontal pivot axis 76 and vertical pivot axis 122, both of which intersect at point 124 on scope axis 20. In this preferred embodiment, then, the scope in essence only pivots about point 124 once the other adjustment clamps are secured. As has been mentioned, joints 74 and 120, also referred to as articulating means, are friction joints and hold the scope in whatever position it is moved to.

Also, since holder 144 is secured directly to the cannula, and not the scope itself, the scope can be repositioned along scope axis 20 by sliding the scope within the cannula. The scope may be removed from apparatus 10 for tip cleaning or x-ray clearance, by withdrawing the scope from the cannula. The cannula remains in position, being held in holder 144. The scope is thus readily reinserted at the same angular position it had prior to removal.

FIGS. 6–12 illustrate a second embodiment preferably usable in place of friction joint 120 and scope holder 144. This embodiment includes a vertical axis pivoting friction joint 160 supporting a support arm 162 relative to a cross bar 164 equivalent to cross bar 112. Arm 162 supports a scope holder 166 that is shown attached to a cannula 168.

Figures 6, 7:
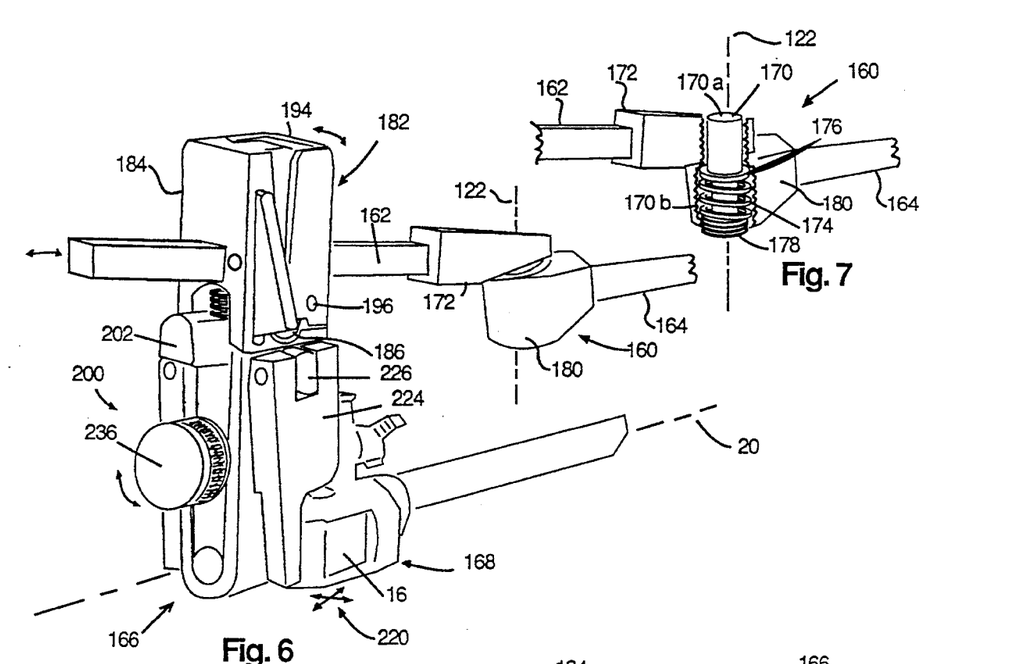
FIG. 6 is an isometric view of second embodiments of the friction vertical pivot joint and scope holder of the embodiment of FIG. 1, shown with the scope holder attached to a cannula.
FIG. 7 is a break-away view of the pivot joint of the embodiment of FIG. 6.

Friction joint 160 is very similar to friction joint 120 except that it is upside down and arm 162 extends upwardly away from the joint preferably at an angle of 20°. The support arm is thus parallel with scope axis 20.

As shown in FIG. 7, joint 160 includes a shaft 170 having an enlarged portion 170a fixedly mounted in an arm base member 172. Shaft 170 also has a reduced diameter portion 170b sized to be freely received in a tension spring 174. Spring 174 is captured between a washer 176, supported on shaft portion 170b against a shoulder formed by enlarged portion 170a, and a tension adjustment screw 178. This screw is threadedly received in a bore in a bar base member 180. As with joint 120, the resistance to movement about vertical pivot axis 122 is controlling by adjusting the tension on spring 174 with screw 178.

Figure 8:
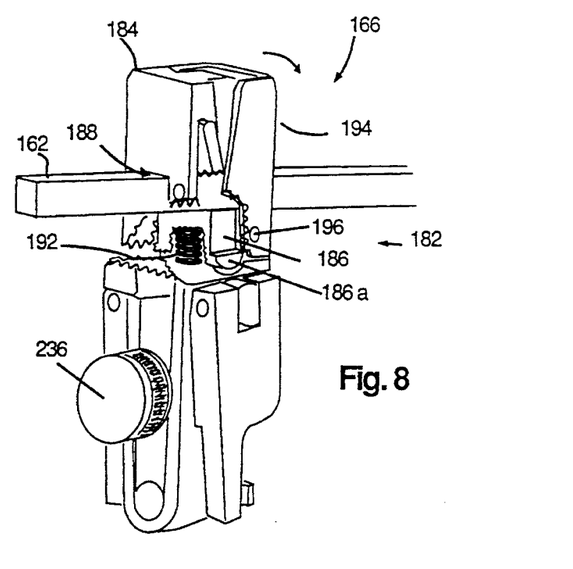
FIG. 8 is a partial break-away view of the scope holder of FIG. 6 showing the arm-lock apparatus for supporting the scope holder relative to an arm extending from the pivot joint.
Figure 9:
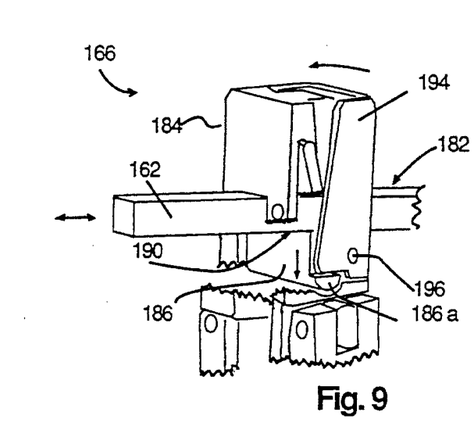
FIG. 9 is a break-away view of a portion of the scope holder of FIG. 8 showing the arm-lock apparatus in a release position.

Referring now to FIGS. 8 and 9, holder 166 includes a support-arm lock assembly 182 mounted in a holder body 184. A lock member 186 is mounted in body 184 for sliding vertically a small distance in a slot, not shown. Body 184 includes a channel 188 for slidingly receiving support arm 162. A recess 190 in the top of the lock member conforms and is generally aligned with channel 188, but is movable slightly upwardly into the channel by action of a biasing spring 192. The upper end of spring 192 extends upwardly into a bore in the lock member and has a lower end that rests in the bottom of the lock member slot in body 184.

During normal use, the lock member is biased upwardly against a support arm supported in channel 188, preventing movement of the support arm. When it is desired to move the scope holder relative to the support arm, the upper end of a lever arm 194 is squeezed toward the top of holder body 184, as shown by the arrow in FIG. 9. Lever arm 194 pivots about a pin 196 mounted on each side of the holder body. This forces a lower edge down against an extension 186a of the lock member. This pushes the lock member down against the force of spring 192, releasing the support arm in the channel. The support arm is then free to be moved to a different position or to be removed from the holder. When the lever arm is released, the lock member reseats against the support arm, locking it in position.

In some cases it is desirable to apply friction to a laparoscope shaft to prevent it from sliding inwardly through an associated cannula and to prevent it from rotating. There are other cases in which it is desirable to allow the laparoscope to be easily moved. Accordingly, and as shown particularly in FIGS. 10 and 11, holder 166 also includes a laparoscope friction assembly 200. This assembly includes a vertical slider 202 seated in a vertical slot 204 in holder body 184. Slider 202 includes an outwardly extending knob 202a at the upper end and has a concave surface 202b at its lower end. This lower surface is disposed in line with a laparoscope channel 206 sized to freely receive the shaft 30 of a laparoscope along axis 20. Slider 202 is biased downwardly toward channel 206 by a bias spring 208 seated in a corresponding bore, not shown, in the upper end of the slider. The other end of the spring is seated against the top surface of slot 204, as shown.

Figures 10, 11, 12:
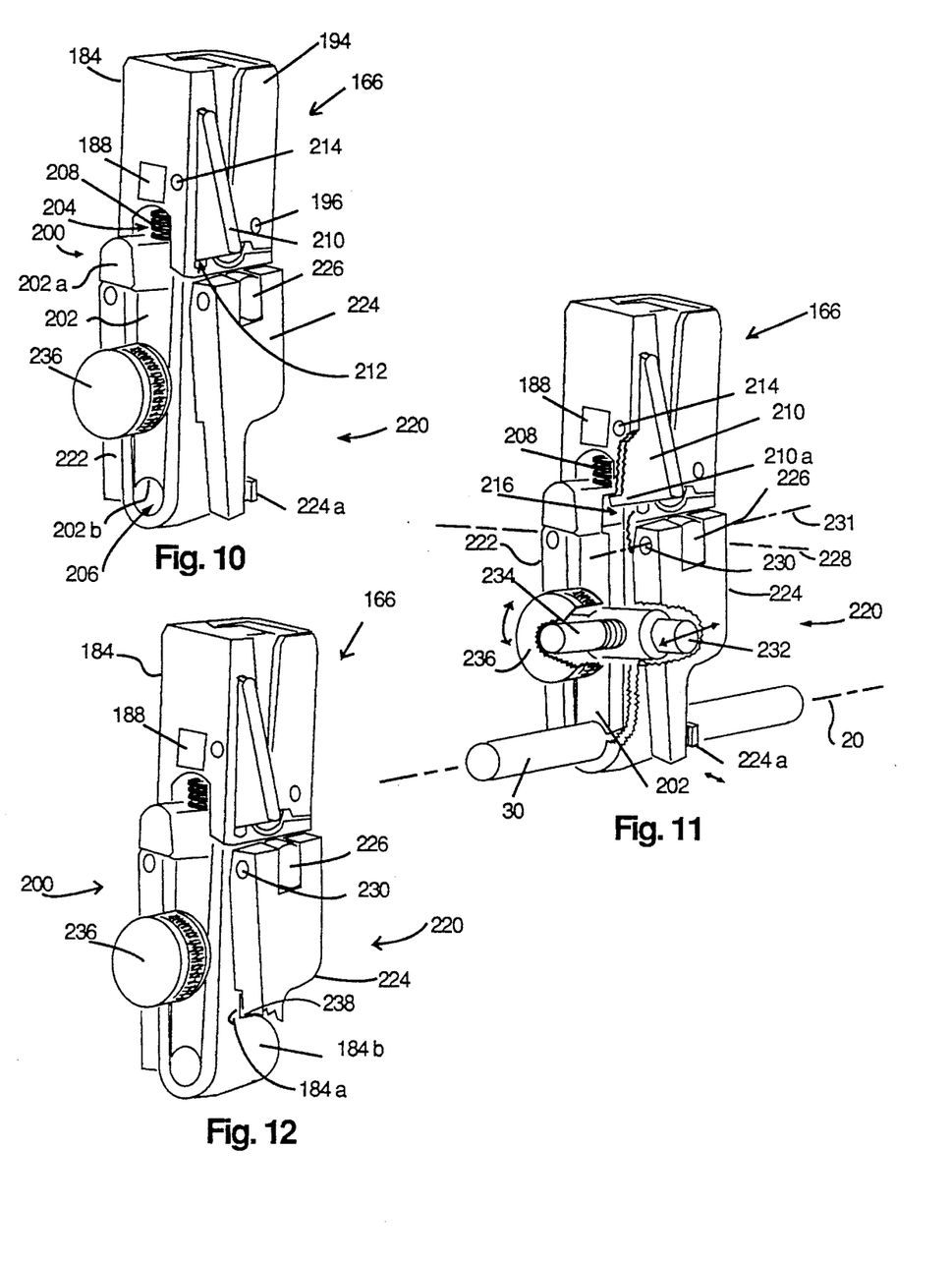
FIG. 10 is an isometric view of the scope holder of FIG. 6 separated from the support arm and cannula.
FIG. 11 is a partial break-away view of the scope holder of FIG. 10 supporting the shaft of a laparoscope.
FIG. 12 is a view of the scope holder of FIG. 10 with a wing for supporting a cannula partially broken away.

When the action of the spring is allowed to act on the slider, frictional pressure is applied to a laparoscope shaft that is sufficient to hold the shaft in longitudinal and rotational position. However, the friction is preferably light enough to allow the laparoscope to be moved by manual manipulation. Friction assembly 200 thus preferably does not function to fixedly lock the scope shaft in position.

For those cases in which it is desired to leave the scope freely movable, a friction defeat lever 210 is provided. Lever 210 is mounted in a slot 212 in the side of the holder body for pivoting about a pin 214. At the inside lower edge of lever 210 is a finger 210a that is movable relative to slider 202, as shown in FIG. 11. The side of the slider has a recess 216 in which finger 210a may be inserted after moving the slider upwardly in slot 204 by manipulation of knob 202a. This then prevents the slider from moving down against the scope shaft. The slider may be released by pressing inwardly on the top of lever 210, and thereby disengaging finger 210a from recess 216.

Finally, holder 166 also preferably includes a cannula holding assembly, such as assembly 220. There are different types of cannulas, and a suitable holder can be readily designed to attach each type to holder 166. The assembly shown is for holding a cannula having side slots or openings in which engaging tabs may be inserted. More particularly, assembly 220 includes wings 222 and 224 positioned on opposite sides of holder body 184. A pivot rod 226 extends through body 184 for pivoting about a lateral axis 228. The wings are suspended from the opposite ends of the pivot rod by a cross pivot pin, such as pivot pin 230 associated with wing 224. The pivot pins allow the bottom ends of the wings to pivot outwardly from the holder body about transverse axes, such as axis 231. Each wing is biased outwardly by a spring, not shown, captured in respective recesses in the wing and holder body.

Further, the positions of the wings are controlled by movement of a laterally extending thrust shaft 232 supported in the holder body. The thrust shaft is itself laterally shiftable in position, generally parallel with support-arm channel 188, by rotation of a threaded drive shaft 234. Shaft 234 is rotated by manual rotation of an enlarged knob 236 mounted on an exposed end. The middle section of the drive shaft is threadedly received in a correspondingly threaded bore in thrust shaft 232. The drive shaft is also positioned in a complementary slot in slider 202 and a bore in the opposite side of holder body 184.

The bottom end of each wing has a corresponding outwardly extending tab, such as tab 224a compatible with the cannula that it is designed to engage. A flare pin, such as pin 238, extends from the inside surface of the lower end of each wing. Knob 236 is rotated to extend tabs 222a and 224a toward a cannula to be attached. The wings are then pressed toward the holder body and the tabs inserted in the corresponding slots of the cannula. With the wings in this position, the flare pins seat in a tapered groove, such as groove 184a. These grooves are deepest near the cannula. As knob 236 is turned in the opposite direction to draw the cannula toward the holder body, the wings are pushed away from the holder body as the flare pins travel in the associated grooves. This further secures the cannula to the holder. Additionally, as the cannula is drawn toward the holder body, a projection 184b of the holder body extending around the opening of scope shaft channel 206, as shown in FIG. 12, presses against the cannula body. This binds the cannula in a grip between the tabs and projection 184b.

Laparoscope holder 166 has an advantage over holder 144 in ease with which it may be positioned on the support arm. That is, it is simply necessary to grasp the top of the holder and squeezing lever 194 against holder body 184. Further, the scope itself, independently of the cannula, can be selectively frictionally secured in the holder. When it is desired to free the scope, simple lever and slide movements are all that are necessary to defeat the function of the friction assembly.

Endoscope holder apparatus 10, with either embodiment of the scope holder, has several beneficial features. The angle and linear position of the scope is adjustable with one operator hand. There is (selectively, in the second embodiment) no restriction to scope removal from or manipulation in the cannula. The overall angular position of the scope and cannula is held by friction controlled springs having adjustable compression.

The simplicity of the intersecting two-axis linkage avoids the need for multi-joint arms that often interfere with scope angular movement and are more difficult to set up and adjust. The friction joints avoid the need to release and reapply locking mechanisms each time the scope is adjusted. This is an activity that typically requires the use of two hands, one to hold and position the scope, and the other to manipulate the lock mechanisms. Where more than one joint or lock mechanism is involved, adjustment is awkward and more time consuming.

Apparatus 10, being a mechanical linkage system, does not require a source of positive or negative air pressure. Mechanisms based on such systems must accordingly be controlled through conduit, valving and switches. The added complexity of such systems is avoided in the preferred embodiments of the present invention.

The two-axis mechanical geometry of the present invention also allows the apparatus to be positioned close to a patient so that it does not interfere with movement of the scope, other instruments or operating personnel, or with viewing of the operating area by the operating personnel.

Variations in form and detail may be made in the preferred embodiment of the present invention without varying from the spirit and scope of the invention as defined in the claims when construed according to applicable legal principles. For instance, the purely mechanical assembly described with reference to the preferred embodiment could be replaced with a positive or negative air pressure system or a computer-controlled system employing air or electricity driven servo motors. Other mechanical linkage configurations could be designed which would provide the effect of nearly intersecting axes. As has been mentioned, the various axes do not have to truly intersect in order to obtain the benefits of the invention. The preferred embodiment is thus provided for purposes of explanation and illustration, but not limitation.

I claim:

1. An endoscope supporting apparatus for supporting an endoscope extending along a scope axis through an incision region corresponding to an incision in a patient positioned adjacent to an external frame comprising:
   a base fixedly mountable on the external frame;
   a holder fixedly mountable to the endoscope for supporting the endoscope with the scope axis extending through the incision region; and
   articulating means coupling said base to said holder for restraining movement of said holder to motion only about a plurality of non-parallel axes that pass through the incision region.

2. An apparatus according to claim 1 wherein the plurality of axes intersect the scope axis.

3. An apparatus according to claim 1 wherein the plurality of axes are orthogonal and intersect.

4. An apparatus according to claim 1 wherein the plurality of axes intersect in the incision region.

5. An apparatus according to claim 1 wherein said articulating means includes a first pivot means for pivoting said holder about a first axis and a second pivot means spaced from said first pivot means for pivoting said holder about a second axis, with both of said first and second pivot means being spaced from the incision region.

6. An apparatus according to claim 1 wherein said holder supports an endoscope externally of the incision region.

7. An apparatus according to claim 1 wherein said articulating means further comprises means for resisting movement about at least one of the plurality of axes when a force is applied to said holder about the at least one axis.

8. An apparatus according to claim 7 wherein said means for resisting movement further comprises means for varying the minimum force.

9. An apparatus according to claim 7 wherein said articulating means further comprises means manually operable in a first state for disabling said means for resisting movement whereby said holder is freely moveable about the at least one axis, and in a second state for enabling said means for resisting movement about the at least one axis.

10. An apparatus according to claim 9 wherein said disabling means, when in said second state, is manually operable at a plurality of distinct positions about the at least one axis.

11. An apparatus according to claim 9 wherein said articulating means includes first and second support bodies and a movement member, both of said first and second support bodies being mounted relative to said movement member for movement about the one axis, said means for resisting movement being structured for resisting movement between said first support body and said movement member, said second support body being freely moveable about the one axis relative to said movement member, and said disabling means comprising means for selectively fixing the position of said second support body relative to said movement member.

12. An apparatus according to claim 1 wherein said articulating means further comprises means for resisting movement about the plurality of axes when forces are applied to said holder about the plurality of axes.

13. An apparatus according to claim 12 wherein said means for resisting movement further comprises means for varying the resistances to movement about the first and second axes.

14. An endoscope supporting apparatus for supporting an endoscope extending through a region containing an incision in a patient positioned on a surgical table having a mounting rail, comprising:

a first clamp fixedly mountable at a position along the mounting rail of the surgical table;

a first arm;

a second clamp for fixedly securing said first arm in a selected vertical position relative to said first clamp and in a selected orientation about a vertical first axis;

a third clamp having a clamp body, said third clamp being mounted on the upper end of said first arm for fixedly securing said clamp body about a horizontal second axis that is orthogonal to the first axis;

a second arm;

a first manually operable pivot means mounted on said clamp body for pivoting said second arm about t third axis that is orthogonal to the first axis when the third axis is horizontal and is orthogonal top the second axis when viewed from a plane parallel to both the second and third axes;

a fourth clamp for fixedly securing said second arm in a selected position along the third axis;

a holder fixedly mountable to the endoscope for holding the endoscope along a scope axis that intersects the third axis at a given point; and a second manually operable pivot means mounted on an end of said second arm spaced from said third clamp and selectively a manually attached to said holder for pivoting said holder relative to said second arm about a fourth axis that is orthogonal to and intersects the third axis at the given point;

whereby an endoscope is manually pivotable about the given point when secured in said holder and said first, second, third and fourth clamps are secured.

* * * * *